United States Patent
Levin et al.

(10) Patent No.: US 12,239,819 B2
(45) Date of Patent: Mar. 4, 2025

(54) METHOD AND SYSTEM TO TREAT ACUTE DECOMPENSATED HEART FAILURE

(71) Applicant: REPRIEVE CARDIOVASCULAR, INC., Milford, MA (US)

(72) Inventors: Howard R. Levin, New York, NY (US); Andrew Halpert, Milford, MA (US); Zoar Engelman, New York, NY (US); Mark Gelfand, New York, NY (US)

(73) Assignee: Reprieve Cardiovascular, Inc., Milford, MA (US)

( * ) Notice: Subject to any disclaimer, the term of this patent is extended or adjusted under 35 U.S.C. 154(b) by 683 days.

(21) Appl. No.: 17/056,387

(22) PCT Filed: May 16, 2019

(86) PCT No.: PCT/US2019/032641
§ 371 (c)(1),
(2) Date: Nov. 17, 2020

(87) PCT Pub. No.: WO2019/222485
PCT Pub. Date: Nov. 21, 2019

(65) Prior Publication Data
US 2021/0236727 A1    Aug. 5, 2021

Related U.S. Application Data

(60) Provisional application No. 62/673,298, filed on May 18, 2018.

(51) Int. Cl.
*A61M 5/172*    (2006.01)
*A61M 5/168*    (2006.01)
(Continued)

(52) U.S. Cl.
CPC ...... *A61M 5/1723* (2013.01); *A61M 5/16804* (2013.01); *G16H 20/17* (2018.01);
(Continued)

(58) Field of Classification Search
CPC ............ A61M 5/1723; A61M 5/16804; A61M 2202/0496
See application file for complete search history.

(56) References Cited

U.S. PATENT DOCUMENTS 3,954,010 A    5/1976    Hilblom
4,132,644 A    1/1979    Kolberg
(Continued)

FOREIGN PATENT DOCUMENTS

| EP | 0258690 | 3/1998 |
|---|---|---|
| EP | 1986007 | 10/2008 |
| EP | 3278833 | 2/2018 |
| EP | 4108171 | 12/2022 |
| GB | 2560580 | 9/2018 |
| JP | 2008110150 | 5/2008 |

(Continued)

OTHER PUBLICATIONS

PCT Search Report and Written Opinion, Appl. No. PCT/US19/32641, dated Mar. 31, 2020, 22 pages.
(Continued)

*Primary Examiner* — Bradley J Osinski
(74) *Attorney, Agent, or Firm* — Perkins Coie LLP

(57) ABSTRACT

A apparatus and method to treat patients with acute decompensated heart failure (ADHF), heart failure or another fluid overload condition, that includes: administrating a diuretic to the patient to increase urine output of the patient; monitoring a rate or amount of urine output by the patient after administration of the diuretic; infusing a hydration liquid into the patient to induce an increase in the urine output; and adjusting the rate or amount of the hydration liquid infused into the patient to achieve a target fluid loss in the patient.

20 Claims, 6 Drawing Sheets

(51) Int. Cl.
  *G16H 20/17*    (2018.01)
  *G16H 40/63*    (2018.01)
  *G16H 50/20*    (2018.01)

(52) U.S. Cl.
  CPC ............ *G16H 40/63* (2018.01); *G16H 50/20* (2018.01); *A61M 2202/0496* (2013.01); *A61M 2205/18* (2013.01); *A61M 2205/50* (2013.01)

(56) References Cited

U.S. PATENT DOCUMENTS

| | | |
|---|---|---|
| 4,146,029 A | 3/1979 | Ellinwood, Jr. |
| 4,204,957 A | 5/1980 | Weickhardt |
| 4,216,462 A | 8/1980 | McGrath et al. |
| 4,229,299 A | 10/1980 | Savitz et al. |
| 4,261,360 A | 4/1981 | Perez |
| 4,275,726 A | 6/1981 | Schael |
| 4,291,692 A | 9/1981 | Bowman et al. |
| 4,343,316 A | 8/1982 | Jespersen |
| 4,411,649 A | 10/1983 | Kamen |
| 4,448,207 A | 5/1984 | Parrish |
| 4,449,538 A | 5/1984 | Corbitt et al. |
| 4,504,263 A | 3/1985 | Steuer et al. |
| 4,658,834 A | 4/1987 | Blankenship et al. |
| 4,712,567 A | 12/1987 | Gille et al. |
| 4,728,333 A | 3/1988 | Masse et al. |
| 4,728,433 A | 3/1988 | Buck et al. |
| 4,813,925 A | 3/1989 | Anderson, Jr. et al. |
| 4,923,598 A | 5/1990 | Schal |
| 4,994,026 A | 2/1991 | Fecondini |
| 5,098,379 A | 3/1992 | Conway et al. |
| 5,176,148 A | 1/1993 | Wiest et al. |
| 5,179,862 A | 1/1993 | Lynnworth |
| 5,207,642 A | 5/1993 | Orkin et al. |
| 5,573,506 A | 11/1996 | Vasko |
| 5,586,973 A | 12/1996 | Lemaire et al. |
| 5,709,670 A | 1/1998 | Vancaillie et al. |
| 5,722,947 A | 3/1998 | Jeppsson et al. |
| 5,769,087 A | 6/1998 | Westphal et al. |
| 5,814,009 A | 9/1998 | Wheatman |
| 5,891,051 A | 4/1999 | Han et al. |
| 5,910,252 A | 6/1999 | Truitt et al. |
| 5,916,153 A | 6/1999 | Rhea, Jr. |
| 5,916,195 A | 6/1999 | Eshel et al. |
| 5,981,051 A | 11/1999 | Motegi et al. |
| 5,984,893 A | 11/1999 | Ward |
| 6,010,454 A | 1/2000 | Arieff et al. |
| 6,171,253 B1 | 1/2001 | Bullister et al. |
| 6,231,551 B1 | 5/2001 | Barbut |
| 6,272,930 B1 | 8/2001 | Crozafon |
| 6,514,226 B1 | 2/2003 | Levin et al. |
| 6,531,551 B2 | 3/2003 | Ohno et al. |
| 6,537,244 B2 | 3/2003 | Paukovits et al. |
| 6,554,791 B1 | 4/2003 | Cartledge et al. |
| 6,640,649 B1 | 11/2003 | Paz et al. |
| 6,740,072 B2 | 5/2004 | Starkweather et al. |
| 6,752,779 B2 | 6/2004 | Paukovits et al. |
| 6,796,960 B2 | 9/2004 | Cioanta et al. |
| 6,827,702 B2 | 12/2004 | Lebel et al. |
| 6,942,637 B2 | 9/2005 | Cartledge et al. |
| 7,029,456 B2 | 4/2006 | Ware et al. |
| 7,044,002 B2 | 5/2006 | Ericson et al. |
| 7,137,964 B2 | 11/2006 | Flaherty |
| 7,278,983 B2 | 10/2007 | Ireland et al. |
| 7,727,222 B2 | 6/2010 | Da Silva |
| 7,736,354 B2 | 6/2010 | Gelfand |
| 7,739,921 B1 | 6/2010 | Babcock |
| 7,758,562 B2 | 7/2010 | Gelfand |
| 7,758,563 B2 | 7/2010 | Gelfand |
| 7,837,667 B2 | 11/2010 | Gelfand |
| 8,007,460 B2 | 8/2011 | Gelfand |
| 8,075,513 B2 | 12/2011 | Rudko et al. |
| 8,233,957 B2 | 7/2012 | Merz et al. |
| 8,444,623 B2 | 5/2013 | Gelfand |
| 8,556,846 B2 | 10/2013 | O'Mahony et al. |
| 8,714,030 B1 | 5/2014 | Liu |
| 9,526,833 B2 | 12/2016 | Gelfand et al. |
| 10,045,734 B2 | 8/2018 | Da Silva |
| 10,537,281 B2 | 1/2020 | Thompson et al. |
| 10,639,419 B2 | 5/2020 | Halpert |
| 11,064,939 B2 | 7/2021 | Da Silva |
| 11,213,621 B2 | 1/2022 | Halpert |
| 11,357,446 B2 | 6/2022 | Levin et al. |
| 11,633,137 B2 | 4/2023 | Conley et al. |
| 11,696,985 B2 | 7/2023 | Halpert |
| 11,950,925 B2 | 4/2024 | Levin |
| 11,986,302 B2 | 5/2024 | Conley et al. |
| 11,992,332 B2 | 5/2024 | Da Silva |
| 2001/0029340 A1 | 10/2001 | Mault et al. |
| 2002/0025597 A1 | 2/2002 | Matsuda |
| 2002/0072647 A1 | 6/2002 | Schock et al. |
| 2002/0107536 A1 | 8/2002 | Hussein |
| 2002/0151834 A1 | 10/2002 | Utterberg |
| 2002/0161314 A1 | 10/2002 | Sarajarvi |
| 2003/0040700 A1 | 2/2003 | Hickle |
| 2003/0048185 A1 | 3/2003 | Citrenbaum et al. |
| 2003/0048432 A1 | 3/2003 | Jeng et al. |
| 2003/0114786 A1 | 6/2003 | Hiller et al. |
| 2004/0025597 A1 | 2/2004 | Ericson et al. |
| 2004/0059295 A1 | 3/2004 | Cartledge et al. |
| 2004/0081585 A1 | 4/2004 | Reid |
| 2004/0087894 A1 | 5/2004 | Flaherty |
| 2004/0122353 A1 | 6/2004 | Shahmirian et al. |
| 2004/0133187 A1 | 7/2004 | Hickle |
| 2004/0163655 A1 | 8/2004 | Gelfand et al. |
| 2004/0167415 A1 | 8/2004 | Gelfand |
| 2004/0167464 A1 | 8/2004 | Ireland et al. |
| 2004/0176703 A1 | 9/2004 | Christensen et al. |
| 2004/0193328 A1 | 9/2004 | Zaitsu et al. |
| 2004/0243075 A1 | 12/2004 | Harvie |
| 2005/0027254 A1 | 2/2005 | Vasko |
| 2005/0065464 A1 | 3/2005 | Talbot et al. |
| 2005/0085760 A1 | 4/2005 | Ware et al. |
| 2006/0052764 A1 | 3/2006 | Gelfand et al. |
| 2006/0064053 A1 | 3/2006 | Bollish et al. |
| 2006/0100743 A1 | 5/2006 | Townsend et al. |
| 2006/0184084 A1 | 8/2006 | Ware et al. |
| 2006/0235353 A1 | 10/2006 | Gelfand et al. |
| 2006/0253064 A1 | 11/2006 | Gelfand et al. |
| 2006/0270971 A1 | 11/2006 | Gelfand et al. |
| 2007/0055198 A1 | 3/2007 | O'Mahony et al. |
| 2007/0088333 A1 | 4/2007 | Levin et al. |
| 2008/0027409 A1 | 1/2008 | Rudko et al. |
| 2008/0033394 A1 | 2/2008 | Gelfand et al. |
| 2008/0051764 A1 | 2/2008 | Dent et al. |
| 2008/0171966 A1 | 7/2008 | Rudko et al. |
| 2008/0221512 A1 | 9/2008 | Da Silva et al. |
| 2009/0054745 A1 | 2/2009 | Jennewine |
| 2009/0062730 A1* | 3/2009 | Woo ............... A61M 5/1723 604/66 |
| 2010/0133510 A1 | 6/2010 | Kim et al. |
| 2010/0185175 A1 | 7/2010 | Kamen |
| 2010/0280443 A1 | 11/2010 | Gelfand et al. |
| 2010/0280444 A1 | 11/2010 | Gelfand et al. |
| 2010/0286559 A1 | 11/2010 | Paz et al. |
| 2011/0046514 A1 | 2/2011 | Greenwald et al. |
| 2011/0046516 A1 | 2/2011 | Paz et al. |
| 2011/0120231 A1 | 5/2011 | Berger |
| 2011/0196304 A1 | 8/2011 | Kramer et al. |
| 2011/0288524 A1 | 11/2011 | Gelfand et al. |
| 2012/0078137 A1 | 3/2012 | Mendels |
| 2012/0259308 A1 | 10/2012 | Gelfand |
| 2013/0104667 A1 | 5/2013 | Koyano |
| 2013/0235691 A1 | 9/2013 | Volker |
| 2013/0261412 A1 | 10/2013 | Reed |
| 2013/0274705 A1 | 10/2013 | Burnes et al. |
| 2014/0031787 A1 | 1/2014 | Burnes et al. |
| 2014/0073973 A1 | 3/2014 | Sexton |
| 2014/0228755 A1 | 8/2014 | Darrah et al. |
| 2014/0260600 A1 | 9/2014 | Rike |
| 2014/0366641 A1 | 12/2014 | Jedema et al. |
| 2015/0105694 A1 | 4/2015 | Mahajan |
| 2015/0233749 A1 | 8/2015 | Wang et al. |

(56) References Cited

U.S. PATENT DOCUMENTS

| | | | |
|---|---|---|---|
| 2015/0258277 A1* | 9/2015 | Halpert | A61M 5/1723 604/503 |
| 2016/0051176 A1 | 2/2016 | Ramos et al. | |
| 2016/0051750 A1 | 2/2016 | Tsoukalis | |
| 2016/0136356 A1 | 5/2016 | Ribble et al. | |
| 2017/0016755 A1 | 1/2017 | Boussange et al. | |
| 2017/0052056 A1 | 2/2017 | Yamasaki et al. | |
| 2017/0290974 A1 | 10/2017 | Tsoukalis | |
| 2018/0071455 A9 | 3/2018 | Halpert | |
| 2018/0085510 A1 | 3/2018 | Halpert et al. | |
| 2018/0110455 A1 | 4/2018 | Chang et al. | |
| 2018/0177945 A1 | 6/2018 | Sims et al. | |
| 2018/0245967 A1 | 8/2018 | Parker et al. | |
| 2018/0280620 A1 | 10/2018 | Reichthalhammer | |
| 2019/0001057 A1 | 1/2019 | Tsoukalis | |
| 2019/0038833 A1 | 2/2019 | Pirazzoli et al. | |
| 2019/0262532 A1 | 8/2019 | Oh et al. | |
| 2019/0321588 A1 | 10/2019 | Burnett | |
| 2020/0230351 A1 | 7/2020 | Kelly et al. | |
| 2020/0324044 A1 | 10/2020 | Gylland et al. | |
| 2020/0360604 A1 | 11/2020 | Kolko et al. | |
| 2020/0284234 A1 | 12/2020 | Niland | |
| 2020/0405955 A1 | 12/2020 | Shah et al. | |
| 2021/0077007 A1 | 3/2021 | Jouret et al. | |
| 2021/0085853 A1 | 3/2021 | Chen et al. | |
| 2021/0128815 A1 | 5/2021 | Byrne et al. | |
| 2021/0162188 A1 | 6/2021 | Cui | |
| 2021/0169408 A1 | 6/2021 | Levin | |
| 2021/0196880 A1 | 7/2021 | O'Mahony et al. | |
| 2021/0244381 A1 | 8/2021 | Sweeney et al. | |
| 2021/0260306 A1 | 8/2021 | Gravenstein et al. | |
| 2021/0283357 A1 | 9/2021 | Leonard | |
| 2021/0298653 A1 | 9/2021 | Woodward et al. | |
| 2021/0369959 A1 | 12/2021 | Abal et al. | |
| 2022/0152302 A1 | 5/2022 | Halpert | |
| 2022/0273213 A1 | 9/2022 | Sokolov | |
| 2022/0288362 A1 | 9/2022 | Porter et al. | |
| 2022/0296406 A1 | 9/2022 | Keelen | |
| 2022/0313158 A1 | 10/2022 | Levin et al. | |
| 2022/0330866 A1 | 10/2022 | Conley et al. | |
| 2022/0330867 A1 | 10/2022 | Conley et al. | |
| 2022/0339622 A1 | 10/2022 | Conley et al. | |
| 2023/0010793 A1 | 1/2023 | Testani | |
| 2023/0414871 A1 | 12/2023 | Halpert | |

FOREIGN PATENT DOCUMENTS

| | | |
|---|---|---|
| JP | 2011520549 | 7/2011 |
| JP | A-2011-520549 | 7/2011 |
| JP | A-2017-536857 | 2/2017 |
| KR | 10-2022-0035738 | 3/2022 |
| WO | WO-1996016685 | 6/1996 |
| WO | WO-1996028209 | 9/1996 |
| WO | WO-1997016220 | 5/1997 |
| WO | WO-1999006087 | 2/1999 |
| WO | WO-2005102441 | 11/2005 |
| WO | WO-2006041496 | 4/2006 |
| WO | WO-2009029899 | 3/2009 |
| WO | WO-2013154783 | 10/2013 |
| WO | WO-2014022422 | 2/2014 |
| WO | WO-2015142617 | 9/2015 |
| WO | WO-2016103256 | 6/2016 |
| WO | WO-2018114794 | 6/2018 |
| WO | WO-2019222485 | 11/2019 |
| WO | WO-2020033752 | 2/2020 |
| WO | WO-2022219578 | 10/2022 |

OTHER PUBLICATIONS

Japanese Office Action mailed Jun. 19, 2023 (with English Translation); Japanese Patent Application No. 2021-514940; 6 pages.
Chinese Office Action mailed Sep. 8, 2023 (with English Translation); Chinese Patent Application No. 201980048123.3; 28 pages.
U.S. Appl. No. 16/544,975, filed Aug. 20, 2019, Levin.
U.S. Appl. No. 18/434,540, filed Feb. 6, 2024, Halpert.
U.S. Appl. No. 16/595,182, filed Mar. 4, 2024, Levin.
U.S. Appl. No. 18/637,340, filed Apr. 16, 2024, Conley et al..
U.S. Appl. No. 18/641,241, filed Apr. 19, 2024, Da Silva.
"2016 ESC Guidelines for the Diagnosis and Treatment of Acute and Chronic Heart Failure—Web Addenda," European Heart Journal, 17 pages.
Abraham Otero, "A New Device to Automate the Monitoring of Critical Patients' Urine Output", Hindawi Publishing Corp, BioMed Research Int'l, vol. 2014, Article ID 587593, 8 pages.
Adams et al., "Executive Summary: HFSA 2006 Comprehensive Heart Failure Practice Guideline," Journal of Cardiac Failure, vol. 12, No. 1, 2006, pp. 10-38.
Adaptec Medical Devices, "Ongoing Access To Real-Time And Accurate Monitoring Of Urine Output Could Improve Management Of Critically Ill Patients," Clinical Literature Review, (2016) 8 pages.
Alison Shepherd, "Measuring and Managing Fluid Balance", Nursing Times, vol. 107, No. 28, pp. 12-16 (Jul. 19, 2011) 5 pages.
Allen et al., "Continuous Versus Bolus Dosing of Furosemide for Patients Hospitalized for Heart Failure," American Journal of Cardiology, 105(12): 1794-1794, 2010.
Antonio Tricoli, "Miniaturized Bio-and Chemical-Sensors for Point-of-Care Monitoring of Chronic Kidney Diseases," Sensors 2018, 18, 942; (Mar. 22, 2018) 18 pages.
Baliga, "Diuretic Therapy for Heart Failure Patients," American College of Cardiology, 75:1178-1195, 2020.
Barbara Lara, "Accurate Monitoring Of Intravascular Fluid Volume: A Novel Application Of Intrathoracic Impedance Measures For The Guidance Of vol. Reduction Therapy," IJC Heart & Vasculature, 8 (2015) pp. 47-51, 5pages.
Bell et al., "Risk of Postoperative Acute Kidney Injury in Patients Undergoing Orthopaedic Surgery—Development and Validation of Risk score and Effect of Acute Kidney Injury on Survival: Observational Cohort Study," BMJ: 2015, 9 pages.
Bouman et al., "Red Blood Cell Transfusion and Furosemide in Cardiac Surgery: Friend and Foe?" The Netherlands Journal of Medicine, Dec. 2012, vol. 70, No. 10, 3 pages.
Brater, "Diuretic Therapy," New England Journal of Medicine, 339:387-395, 1998.
Cosgrove III et al., "Automated Control Postoperative Hypertension: A Prospective Randomized Multicenter Study," 1989 by The Society of Thoracic Surgeons, 6 pages.
David Farcy, "Review: Pitfalls in Using Central Venous Pressure as a Marker of Fluid Responsiveness," Emergency Medicine. Jan. 2016;48(1): 18-28, 15 pages.
Ellison et al., "Diuretic Treatment in Heart Failure," New England Journal of Medicine, 377:1964-1975, 2017.
Farkas, "Deresuscitation: Dominating the Diuresis," The Internet Book of Critical Care, 43 p. 2020.
Furutani et al., "An Automatic Control System of the Blood Pressure of Patients Under Surgical Operation," International Journal of Control, Automation, and Systems, vol. 2, No. 1, Mar. 2004, pp. 39-54.
Gheorghiade et al., "Current Medical Therapy for Advanced Heart Failure," American Heart Journal, Jun. 1998, pp. S231-S248.
Goren et al., "Perioperative Acute Kidney Injury," British Journal of Anaesthesia, 2015, 12 pages.
Hasselblad et al., "Relation Between Dose of Loop Diuretics and Outcomes in a Heart Failure Population: Results of the ESCAPE Trial", European Journal of Heart Failure, 9(10):1064-1069, 2007.
Kambiz Kalantari, "Assessment Of Intravascular Volume Status and Volume Responsiveness In Critically Ill Patients," Kidney International (2013) 83, 1017-1028 (Jan. 9, 2013) 12 pages.
Kolh, "Renal Insufficiency After Cardiac Surgery: A Challenging Clinical Problem," European Heart Journal, 2009, pp. 1824-1827.
Kui Jin et al., "Intensive Monitoring of Urine Output Is Associated With Increased Detection of Acute Kidney Injury and Improved Outcomes," Chest Journal—Original Research Critical Care, 152#5, pp. 972-979 (Nov. 2017) 8 pages.
Lassnigg et al., "Lack of Renoprotective Effects of Dopamine and Furosemide During Cardiac Surgery," J. Am Soc Nephrol, 2000, pp. 97-104.

(56) References Cited

OTHER PUBLICATIONS

Lenihan et al., "Trends in Acute Kidney Injury, Associated Use of Dialysis and Mortality After Cardiac Surgery, 1999 to 2008," Ann Thorac Surg. 2013, 17 pages.
Marenzi et al., "Prevention of Contrast Nephropathy by Furosemide With Matched Hydration," JACC: Cardiovascular Interventions, 5(1):90-97, 2011.
Mayo Clinic, "Creatinine Test", Mayo Foundation for Medical Education and Research (MFMER) (downloaded Aug. 16, 2018).
Meersch et al., "Perioperative Acute Kidney Injury: An Under-Recognized Problem," vol. 125, No. 4, www.anesthesia-analgesia.org, Oct. 2017, pp. 1223-1232.
Mendeley et al., "Furosemide", Science Direct, 5 pages, 2016.
Oh et al., "Loop Diuretics in Clinical Practice," Review: Electrolyte Blood Press, 13(1): 5 pages, 2015.
Olivero et al., "Acute Kidney Injury After Cardiovascular Surgery: An Overview," debakeyheartcenter.com/journal, 2012, pp. 31-36.
Palazzuli et al. "Continuous versus bolus intermittent loop diuretic infusion in acutely decompensated heart failure: a prospective randomized trial," Critical Care 18, 2014.
Phillips et al., "Measurement of sodium ion concentration in undiluted urine with cation-selective polymeric membrane electrodes after the removal of interfering compounds", Talanta, Elsevier, Amsterdam, NL, vol. 74, No. 2, Nov. 15, 2007, pp. 255-264.
Prandota et al., "Pharmacokinetics and metabolism of furosemide in man," European Journal of Drug Metabolism and Pharmcokinetics, 1(4): 5 pages, 1976.
Rosenberg et al., "Combination Therapy with Metolazone and Loop Diuretics in Outpatients with Refactory Heart Failure: An Observational Study and Review of the Literature," Cardiovascular Drugs and Therapy, Kluwer Academic Publishers, vol. 19, No. 4, Aug. 2005, 6 pages.
Rui Geng et al., "Identification of Modifiable Risk Factors for Acute Kidney Injury After Coronary Artery Bypass Graft Surgery in an Asian Population," The Journal of Thoracic and Cardiovascular Surgery, Apr. 2014, pp. 1356-1361.
Se Won Oh et al., "Loop Diuretics In Clinical Practice", Electrolytes & Blood Pressure, www.ncbi.nlm.nih.gov/pmc/articles/PMC4520883, printed Mar. 25, 2019, 6 pages.
Stickler et al., "A Sensor To Detect the Early Stages in the Development of Crystalline Proteus mirabilis Biofilm on Indwelling Bladder Catheters", Journal of Clinical Microbiology, Apr. 2006, p. 1540-1542.
Teixeira et al., "Fluid Balance and Urine vol. are Independent Predictors of Mortality in Acute Kidney Injury", Critical Care 17:R14 (2013) 11 pages.
Testani et al., "Rapid and Highly Accurate Prediction of Poor Loop Diuretic Natriuretic Response in Patients with Heart Failure," Circulation; Heart Failure, vol. 9. No. 1, 2016, 32 pages.
Thakar, "Perioperative Acute Kidney Injury," Advances in Chronic Kidney Disease, vol. 20, No. 1, 2013, pp. 67-75.
Unknown Author, "Furosemide Drug Summary," Prescriber's Digital Reference, pp. 1-31, 2016.
Vellinga et al., "Identification of Modifiable Risk Factors for Acute Kidney Injury After Cardiac Surgery," The Netherlands Journal of Medicine, vol. 70, No. 10, Dec. 2012, pp. 450-454.
Vivane Conradds, "Sensitivity And Positive Predictive Value Of Implantable Intrathoracic Impedance Monitoring As A Predictor Of Heart Failure Hospitalizations: The SENSE-HF Trial," European Heart Journal (2011) 32, 2266-2273, 8pages.
Yeh et al., "Goal-directed diuresis: A case-control study of continuous furosemide infusion in critically ill trauma patients", The Journal of Emergencies, Trauma, and Shock, 8(1): 34-38, 2015.
European Office Action and Extended Search Report for European Patent Application No. 19790336.2, Applicant: Reprieve Cardiovascular, Inc., mailed Dec. 18, 2023, 10 pages.
Written Opinion of the International Searching Authority for PCT Application No. PCT/US2005/008948 dated Oct. 3, 2006, 3 pages.
Written Opinion of the International Searching Authority for PCT Application No. PCT/US2007/021791 dated May 8, 2008, 7 pages.
Written Opinion of the International Searching Authority for PCT Application No. PCT/U20S07/009685 dated Jul. 18, 2008, 10 pages.
Written Opinion of the International Searching Authority for PCT Application No. PCT/US2007/009684 dated Jul. 21, 2008, 7 pages.
Written Opinion of the International Searching Authority for PCT Application No. PCT/US2008/007845 dated Sep. 17, 2008, 5 pages.
Written Opinion of the International Searching Authority for PCT Application No. PCT/US2008/007841 dated Sep. 18, 2008 4 pages.
Written Opinion of the International Searching Authority for PCT Application No. PCT/US2007/009683 dated Nov. 24, 2008, 6 pages.
Written Opinion of the International Searching Authority for PCT Application No. PCT/US2009/002739 dated Jun. 19, 2009, 4 pages.
Written Opinion of the International Searching Authority for PCT Application No. PCT/US2010/000137 dated Mar. 16, 2010, 8 pages.
Written Opinion of the International Searching Authority for PCT Application No. PCT/US2015/020196, dated Jun. 12, 2015, 5 pages.
Bart et al., "Ultrafiltration in Decompensated Heart Failure With Cardiorenal Syndrome", The New England Journal of Medicine, Dec. 13, 2012, 9 pages, Massachusetts Medical Society.
Brezis et al., Hypoxia of the Renal Medulla—Its Implications for Disease, New England Journal of Medicine, vol. 322, No. 10, Mar. 9, 1995, 9 pages.
Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, 10 pages.
Dorval et al., "Feasibility Study of the RenalGuard™ Balanced Hydration System: A Novel Strategy for the Prevention of Contrast-Induced Nephropathy in High Risk Patients", International Journal of Cardiology, 2011, 5 pages, Elsevier Ireland Ltd.
Edelson et al., Pharmacokinetics of Iohexol, a New Nonionic Radiocontrast Agent, in Humans, Journal of Pharmaceutical Sciences, vol. 73, No. 7, Jul. 1984, 3 pages.
Felker et al., "Diuretic Strategies in Patients With Acute Decompensated Heart Failure", The New England Journal of Medicine, Mar. 3, 2011, vol. 364, No. 9, 9 pages.
Gloor, James M. and Vincente E. Torres, Reflux and Obstructive Nephropathy, Atlas of Diseases of the Kidney, on-line edition, vol. Two, Section I, Ch. 8, pp. 8.1-8.25, 1999, 27 pages.
Hvistendahl et al., Renal Hemodynamic Response to Gradated Ureter Obstruction in the Pig, Nephron 1996, 74:168-74, 7 pages.
Lelarge et al., Acute Unilateral Renal Failure and Contralateral Ureteral Obstruction, American Journal of Kidney Diseases, vol. XX, No. 3, Sep. 1992, 3 pages.
Levin et al. High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, 1 page.
Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, 161 pages.
Marenzi et al.. "Prevention of Contrast Nephropathy by Furosemide With matched Hydration. The MYTHOS (Induced Diuresis With Matched Hydration Compared to Standard Hydration for Contrast Induced Nephropathy Prevention) Trial", JACC: Cardiovascular Interventions, vol. 5, No. 1, 2012 The American College of Cardiology Foundation, 8 pages.
Mawer et al., "Value of Forced Diuresis in Acute Barbiturate Poisoning", Jun. 29, 1968, British Medical Journal, 2, 4 pages.
Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, 7 pages.

(56) References Cited

OTHER PUBLICATIONS

Pederson et al., Renal Water and Sodium Handling During Gradated Unilateral Ureter Obstruction, Scand J. Urol Nephrol, 2002, 36:163-72, 11 pages.

Rihal et al., Incidence and Prognostic Importance of Acute Renal Failure After Percutaneous Coronary Intervention, Circulation, May 14, 2002, 6 pages.

Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5, 4 pages.

S215 Ultra Low Profile Single Point Load Cell-Strain Guage Sensors and Load Cells, Ultra-Low Profile Single Point Load Cell-S215, http://smdsensors.com/detail_pgs/s215.htm 2005, 3 pages.

Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21, 5 pages.

Stevens, Melissa A., Md et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, 9 pages.

Stevenson et al., "Editorial Comment, Torrent or Torment From the Tubules?", Challenge of the Cardiorenal Connections, Journal of the American College of Cardiology, vol. 45, No. 12, 2005, 4 pages.

Wakelkamp et al., The influence of drug input rate on the development of tolerance to frusemide, Br. J. Clin. Pharmacol 1998, 46:479-487, 9 pages.

Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415, pages.

Doty et al., Effect of Increased Renal Venous Pressure on Renal Function, The Journal of Trauma: Injury, Infection and Critical Care, vol. 47, No. 6, Dec. 1999, 4 pages.

Heyman et al., Pathophysiology of Radiocontrast Nephropathy: A Role for Medullary Hypoxia, Investigative Radiology, vol. 34, No. 11, Nov. 1999, 7 pages.

\* cited by examiner

METHOD AND SYSTEM TO TREAT ACUTE DECOMPENSATED HEART FAILURE

RELATED APPLICATIONS

The present application is a 35 U.S.C. § 371 U.S. National Phase application of International Application No. PCT/US2019/032641, filed May 16, 2019, which claims priority to U.S. Provisional Application 62/673,298, filed May 18, 2018, each of which is incorporated herein by reference in its entirety.

FIELD OF THE INVENTION

The field of the invention is treatment of heart failure and particularly acute decompensated heart failure (ADHF). The invention relates to managing a patient's fluid levels to treat heart failure in general and specifically to treat ADHF.

BACKGROUND OF THE INVENTION

Acute decompensated heart failure (ADHF) is a sudden worsening of the signs and symptoms of heart failure. Symptoms of ADHF often include difficulty breathing, swelling of the legs or feet, and fatigue. ADHF is a common and potentially serious cause of acute respiratory distress. Patients suffering from ADHF are often hospitalized. A characteristic of ADHF is fluid volume overload in a patient.

Reducing fluid volume in a patient is typically an objective of treatment for ADHF. The fluid volume should be reduced in a rapid, safe and effective manner to reduce fluid levels (decongestion) in the patient. Treatment for ADFH conventionally consists of reducing the patient's fluid level with diuretics to cause the patient to urinate. The diuretics may be introduced by an intravenous (IV) line. If treatments with diuretics are unsuccessful, ultra-filtration may be used to reduce fluid level to treat ADFH.

Similar to reducing fluid levels to treat ADFH, fluid removal in patients with heart failure is used to decongest the patient. Fluid levels are reduced to preferably bring the levels back to normal levels for both intravascular and extravascular fluid in the patient. However, it is often not practical to reach normal levels for heart failure patients. Thus, treatments are often performed to reduce these levels to as much as is practical for the patient. These much as is practical levels may remove fluid up to levels where the remaining amount of intravascular fluid in the patient is at or near the minimum required to allow adequate perfusion of the vital organs. These as much as practical levels may still be at conditions where the patient has significant extravascular fluid/total body fluid overload.

Diuretics are an effective method of fluid removal in patients with both acute decompentated (ADHF) and chronic heart failure (HF). The choice of type, amount and timing of diuretics used depend on the stage or presentation of HF or ADHF.

The short-term effects of diuretic administration on urine production for an individual are not entirely predictable. In response to a dose of a diuretic, a patient may produce much less urine than expected which may prolong a hospital stay or cause an outpatient to be hospitalized. Another patient may respond to a dose of diuretic by producing excessive amounts of urine which raises concerns of hypotension and vital organ damage in the patient.

The potential for substantially different responses and treatment outcomes in response to a dosage of diuretics creates uncertainties for physicians who have to determine correct diuretic dosing for an individual patient based on the patient's clinical signs and symptoms. Physicians may prescribe a conservative (low) diuretic dosage and later slowly increase the dose to achieve a desired urine output. This conservative approach can prolong the treatment and may render the patient unable to produce sufficient amounts of urine. Disadvantages of the conservative approach are that the patient's symptoms may be prolonged and the underlying clinical state may worsen due to the slow application of diuretics.

SUMMARY OF THE INVENTION

The inventors conceived of, tested and disclose herein a novel treatment of ADHF and HF in which diuretics are combined with a fluid management device, such as the RenalGuard® system, to promote urine output by injecting fluids into the patient. This treatment is counterintuitive in that it adds fluid to treat a fluid overload condition. Adding fluid would initially appear to make the condition worse. However, the fluid is added to promote high rates of urine output and avoid dehydrating a patient. The injection of the fluid is controlled by monitoring urine output and using urine output as feedback to control the amount of fluid added to the patient. The fluid management device controls the amount of fluid added to the patient such that there is a net reduction in the amount of fluid in the patient. The fluid management device also detects if the patient is not producing sufficient amounts of urine in response to diuretics and then automatically stops fluid injection and issues an alert suggesting that other treatments, such as ultrafiltration, may be appropriate. Use of the fluid management system reduces any risk that a patient will become hypotensive or otherwise suffer problems associated with unnaturally low intravascular fluid levels. Because the use of the fluid management system reduces the risk of a patient becoming hypotensive, physicians are able to prescribe higher doses of a diuretic that should more rapidly reduce fluid levels in a patent than is practical or recommended with diuretic only treatments.

In one embodiment, the invention is embodied in a therapy regimen(s) that includes:

(a) an initial therapy that may include the highest guideline recommended dose of a diuretic. The highest dose may be prescribed to prevent under-diuresis and to achieve a clinically significant amount of volume removal in a period shorter than is often needed for diuretic only treatment regimens. Using a high diuretic dosage should cause urine output that achieves both reductions in hemodynamic conditions (intravascular and extravascular fluid) and therapeutically desirable clinical responses (resolution of symptoms).

(b) monitor the patient's response to the high diuretic dosage for several hours, such as four (4) hours, and determine whether the patient is: (1) responding well to the diuretic by producing sufficient urine output, (2) producing some urine but in an insufficient amount, and (3) producing such a small amount of urine that a different treatment is warranted.

(c) Patients responding well to the high diuretic dosage may be treated without resorting to a fluid management device. Patients producing some urine but in an insufficient amount may be treated with a fluid management device in combination with the high dose of the diuretic. The fluid management system, when combined with diuretics, promote urine output by infusing, at least temporarily, liquids into the patient's vascular system to prompt the kidneys to produce urine. Once the kidneys are prompted, they may continue to produce urine at a relatively high rate even as the amount of fluid being infused is reduced. Patients producing only a small amount of urine may be switched to another treatment such as using inotropic medications, continuous renal replacement therapy (CRRT) or ultra-filtration (UF).

In an embodiment, a patient fluid management system for treating patients with acute decompensated heart failure (ADHF), heart failure or another fluid overload condition, includes means for administrating a diuretic to a patient to increase urine output of the patient; means for monitoring a rate or amount of urine output by the patient after administration of the diuretic; means for infusing a hydration liquid into the patient to induce an increase in the urine output; and a subsystem for adjusting the rate or amount of the hydration liquid infused into the patient based on the actual rate or amount of urine output in order to achieve a target fluid loss in the patient. The subsystem includes a computer control system adapted for evaluating the rate or amount of urine output by the patient, and controlling the means for infusing the hydration liquid to infuse the rate or amount of the hydration liquid to induce the increase in the urine output, and to adjust the rate or amount of the hydration liquid to achieve the target fluid loss in the patient.

In the patient fluid management system, the computer control system may be further adapted for reducing the rate or amount of the liquid infused in response to a urine output exceeding a threshold urine rate or amount, and/or further adapted for reducing or stopping the infusion of the liquid in response to urine output being below a minimum threshold urine rate or amount.

In an embodiment, a patient fluid management system for treating patients with ADHF, heart failure or another fluid overload condition, includes means for administrating a diuretic to a patient to increase urine output of the patient; means for monitoring a rate or amount of urine output by the patient after administration of the diuretic; means for infusing a hydration liquid into the patient; means for determining a central venous pressure of the patient while monitoring the urine output; and a subsystem for adjusting the rate or amount of the hydration liquid infused into the patient based on the CVP.

In the patient fluid management system, the means for determining the CVP may estimate the CVP. The subsystem may be adapted to adjust the rate of the infusion of the hydration liquid if the CVP is outside of a range of CVPs and maintain the rate if the CVP is within the range. The subsystem may be adapted to increase the rate of the infusion if the CVP is below the range and to decrease the rate of the infusion if the CVP is above the range. The subsystem may be adapted to reduce or stop the infusion of the liquid in response to urine output being below a minimum threshold urine rate or amount.

In an embodiment, a fluid management system includes a urine collect device to collect urine from a patient; a pump to pump a hydration liquid into the patient; a measurement system to measure the urine collected and the hydration liquid pumped into the patient; a computer control system to receive information regarding the collected urine and to issue commands to control a rate at which the hydration liquid is pumped into the patient. The rate is determined by the computer control system to achieve a target fluid reduction in the patient.

The measurement system may include at least one weight scale. The computer control system may be configured to calculate fluid reduction in the patient. The fluid reduction in the patient may be calculated as a difference between an amount of the hydration liquid into the patient and an amount of urine from the patient. The computer control system may be configured to receive information regarding fluid delivered to the patient by another source. The information regarding fluid delivered to the patient by another source may be used to calculate the fluid reduction in the patient. The computer control system may be configured to control the rate at which the hydration liquid is pumped into the patient to be an initial level and then reduced. The computer control system may be is configured to reduce the rate at which the hydration liquid is pumped into the patient after determining that the patient is producing urine in excess of a threshold urine rate or amount. The computer control system may be configured to stop pumping the hydration liquid into the patient after determining that the patient is not producing enough urine. The computer control system may be configured to generate an alert to indicate that the patient is not producing enough urine. The computer control system may be configured to determine central venous pressure (CVP). The determination of the CVP may be estimated. The computer control system may be configured to adjust the rate at which the hydration liquid is pumped into the patient when the CVP is outside of a range of CVPs and maintain the rate when the CVP is within the range. The rate at which the hydration liquid is pumped into the patient may be increased when the CVP is below the range and decreased when the CVP is above the range.

In an embodiment, a method to treat patients with ADHF, heart failure or another fluid overload condition, includes monitoring a rate or amount of urine output by the patient after administration of the diuretic; determining a CVP of the patient while monitoring the urine output; and infusing a hydration liquid into the patient based on the CVP.

In an embodiment, a method to treat patients with ADHF, heart failure or another fluid overload condition, includes administrating a diuretic to the patient to increase urine output of the patient; monitoring a rate or amount of urine output by the patient after administration of the diuretic; infusing a hydration liquid into the patient to induce an increase in the urine output; and adjusting the rate or amount of the hydration liquid infused into the patient to achieve a target fluid loss in the patient.

The method may include reducing the rate or amount of the liquid infused in response to a urine output exceeding a threshold urine rate or amount; reducing or stopping the infusion of the liquid in response to urine output being below a minimum threshold urine rate or amount; and/or diagnosing the patient as suffering from ADHF.

In an embodiment, a method to treat patients with ADHF, heart failure or another fluid overload condition, includes administrating a diuretic to the patient to increase urine output of the patient; monitoring a rate or amount of urine output by the patient after administration of the diuretic; determining a CVP of the patient while monitoring the urine output; and infusing a hydration liquid into the patient based on the CVP.

The method of may include determining the CVP by estimating; adjusting a rate of the infusion of the hydration liquid if the CVP is outside of a range of CVPs and maintaining the rate if the CVP is within the range; increasing the rate of the infusion if the CVP is below the range and decreasing if the CVP is above the range; reducing or stopping the infusion of the liquid in response to urine output being below a minimum threshold urine rate or amount; and/or diagnosing the patient as suffering from ADHF.

DETAILED DESCRIPTION OF THE INVENTION

Figure 1:
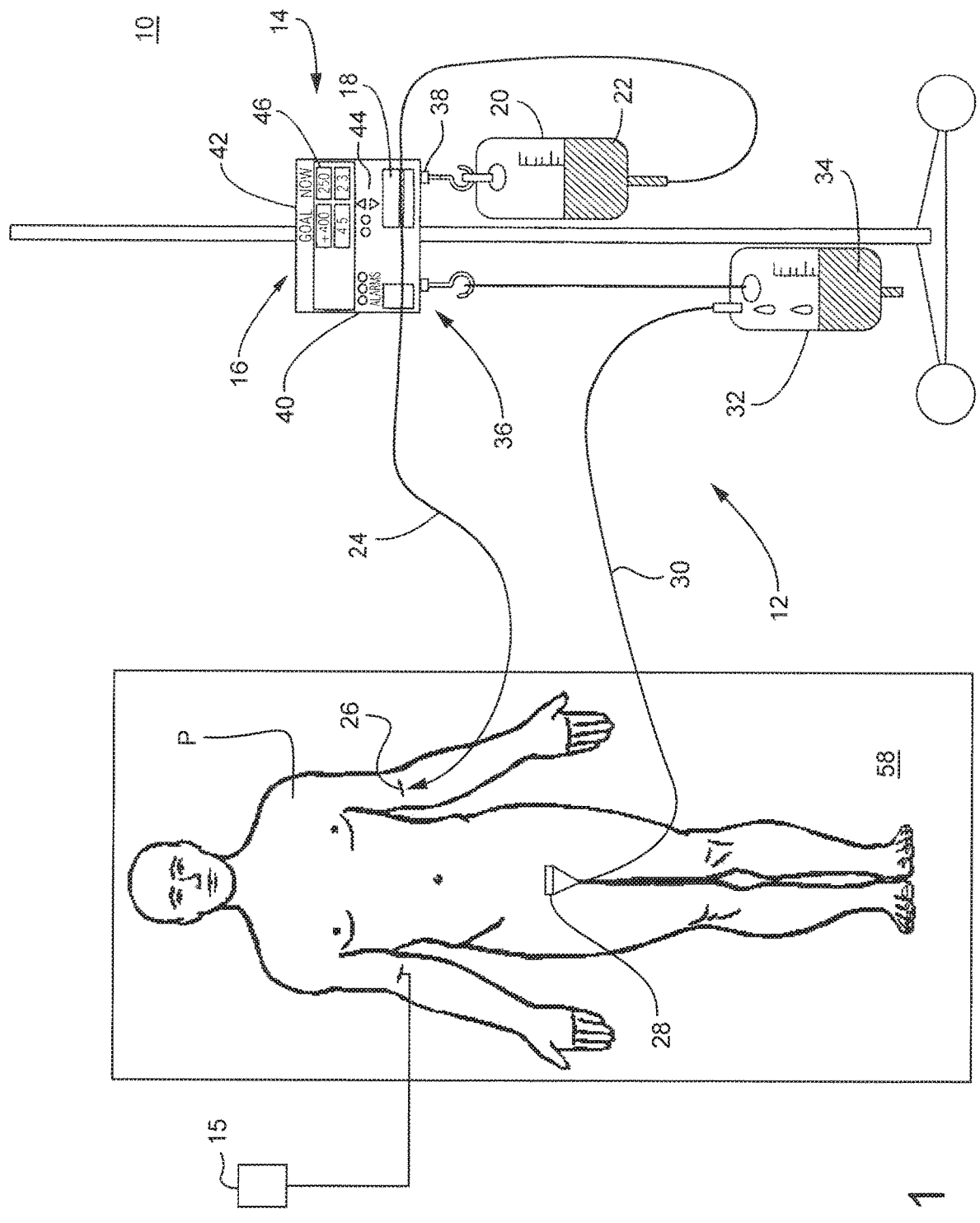
FIG. 1 is a schematic view of one embodiment of a patient hydration system which is configured to monitor urine output and control the injection of a fluid into a patient.

FIG. 1 shows a patient fluid management system 10 that includes a urine collection system 12 and a hydration fluid infusion system 14 both of which are connected to patient P. The patient is suffering from ADFH and may be hospitalized and receiving diuretics 15 through an intravenous (IV) line. The diuretics 15 may be added to a line injecting the hydration fluid or may be added to another saline solution filled bag connected to the patient via another IV line.

The hydration fluid infusion system 14, also referred to as a fluid management system, includes an infusion controller 16, that includes an infusion pump 18, e.g., a peristaltic pump, connected to a fluid source 20, e.g., saline bag, of an hydration fluid 22, e.g. saline, by tubing (line) 24. An intravenous (I.V.) needle 26 is inserted in a vein of the patient P and is connected to infusion pump 18 via tubing 24. Fluid 22 from the source 20 flows through the tubing 24 and I.V. needle 26 directly into a blood vessel, e.g., peripheral vein, of the patient P. The amount or rate of fluid(s) 22 flowing into the patient may be determined by the pumping rate or number of rotations the infusion pump 18.

The urine collection system 12 includes a catheter 28, such as a Foley catheter, placed in the bladder of patient P. Tubing 30 connects catheter 28 to a urine collection device, such as a bag 32. The urine 34 collected in the bag 32 is weighed or otherwise measured by a weight scale 36 or other urine flow measurement device which communicates with the infusion controller 16. A weight scale 38 may also weight the hydration fluid 22.

The amount or rate of urine 34 is monitored in real time by the infusion controller 16. Similarly, the amount of hydration fluid 22 in the fluid source 20 may be monitored or measured by a weight scale 38. The weight scales 36, 38 may be a single weight scale which measures the combined change in urine output and fluid input by and to the patient. The combined change in urine output and fluid input indicates the net fluid loss or gain by the patient.

The infusion controller 16 monitors the weight of the hydration fluid 22, the amount of the hydration fluid 22 pumped through pump 18 or otherwise monitors, in real time, the amount or rate of hydration fluid 22 flowing into the patient P.

The fluid management system 10 may be the RenalGuard System®, developed and marketed by RenalGuard Solutions, Inc. of Milford, Massachusetts, which in the past has been used to protect patients from kidney injury during procedures that require iodinated contrast agents.

A computer control system 40 in the infusion controller 16 receives an input as to a desired negative fluid balance, and/or amount(s) or rate(s) of urine output and/or of a desired amount(s) or rate(s) of a difference of urine output and amount of hydration fluid. A negative fluid balance refers to injecting less hydration fluid 22, in terms of mass or flow rate, into the patient than the amount of urine 34 output. The fluid balance may be repeatedly determined, such as every thirty minutes, every hour or every few hours. During the treatment period, the amount of hydration fluid injected into the patient may initially be greater than the amount of urine output, in an effort to start a high urine output flow. Later in the treatment period, such as after the urine output flow reaches a predetermined high threshold rate, the rate of infusion of the hydration fluid may be reduced. The high urine output flow is expected to continue after the reduction of the rate of the hydration fluid.

The computer control system 40 may include a processor(s) and a non-transient memory configured to store program instructions, settings for the patient fluid management system 10 and data collected from or calculated by the computer control system 40. The data may include urine output volume or rate of urine output, amount of fluid infused into the patient and rate of infusion, the amount and rate of injection of a diuretic, the weight of the patient at various times during the infusion of the fluid, and the time during which the patient is treated with the patient fluid management system 10. The computer control system 40 may include a console 42 having a user input device 44, such as a key pad, and a user output device 46, such as a computer display.

The input device 44 may be used to input certain parameters of the treatment sessions, such as a desired fluid balance level, desired urine output level, and the planned duration of the input balance level or urine output level. Another input may be the amount of fluids during the treatment session received by the patient through means other than the fluid source 20. For example, the input device 44 may be configured to receive inputs indicating the amount of fluid included with a saline filled bag used to inject the diuretic 15 into the patient.

Figure 2:
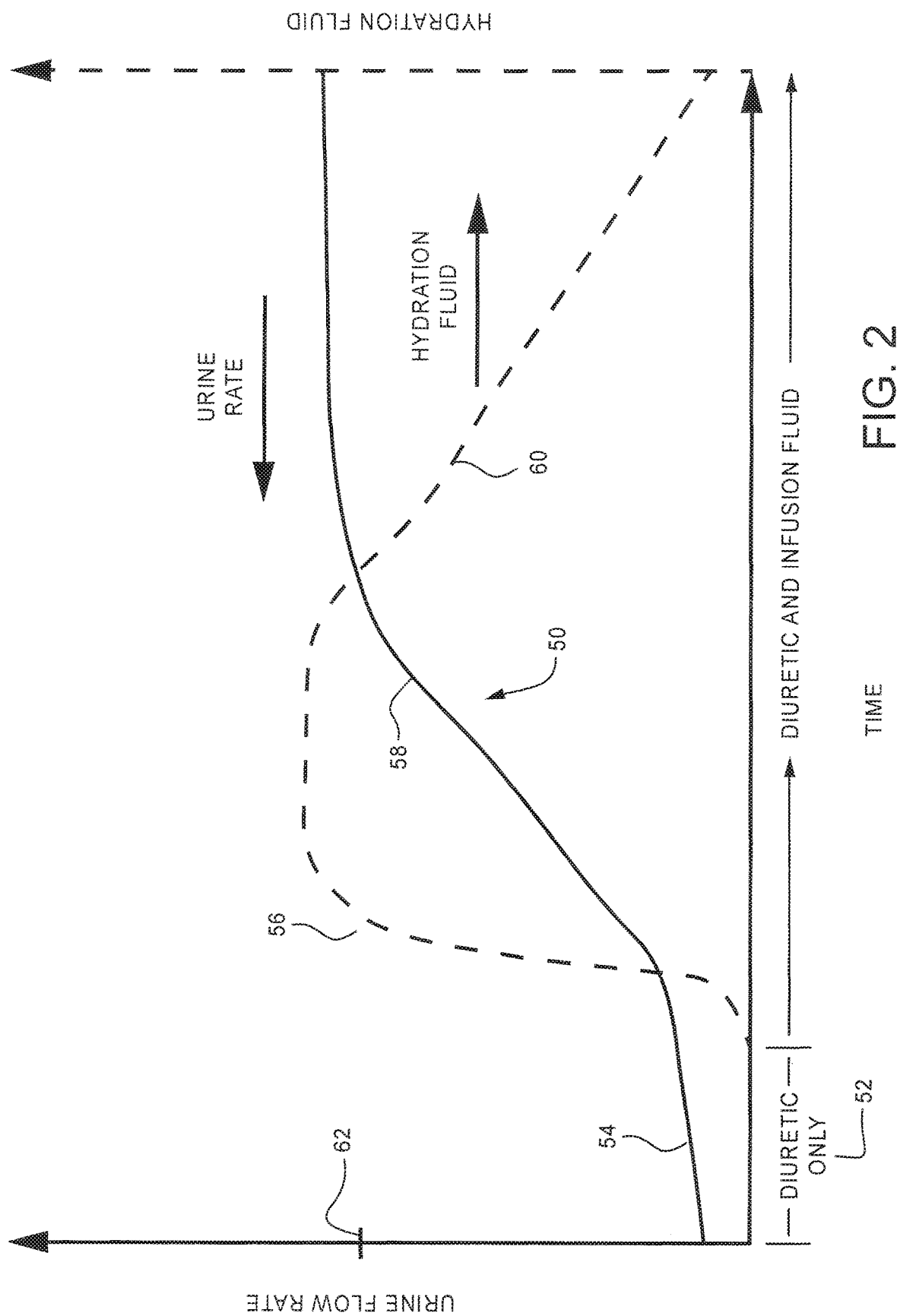
FIG. 2 is a graphical representation showing a time line of desired urine flow rate achieved with the fluid management system before, during and after an event such as cardiac surgery.

FIG. 2 is a graphical representation showing a time line of an exemplary urine flow rate 50 and rate of hydration fluid 52 over a period of a treatment session. During an initial period 54, a diuretic is injected into the patient and there may be no infusion of a hydration fluid. During this initial period, the urine flow rate is low and thus a determination is made to infuse a hydration fluid 22 into the patient. The hydration fluid 22 is infused initially at a high rate 56. In response to the diuretic and the infusion of the hydration fluid, the urine output rate should increase at a relatively rapid rate 58. Once the urine output rate has reached an acceptably high rate 62, the fluid monitoring system may reduce 60 the rate of hydration fluid to a lower rate or to zero. It is expected that the high urine output will remain high after the reduction in the rate of the hydration fluid. The high rate of urine output should continue as the body of the patient generates a net fluid loss.

Figure 3:
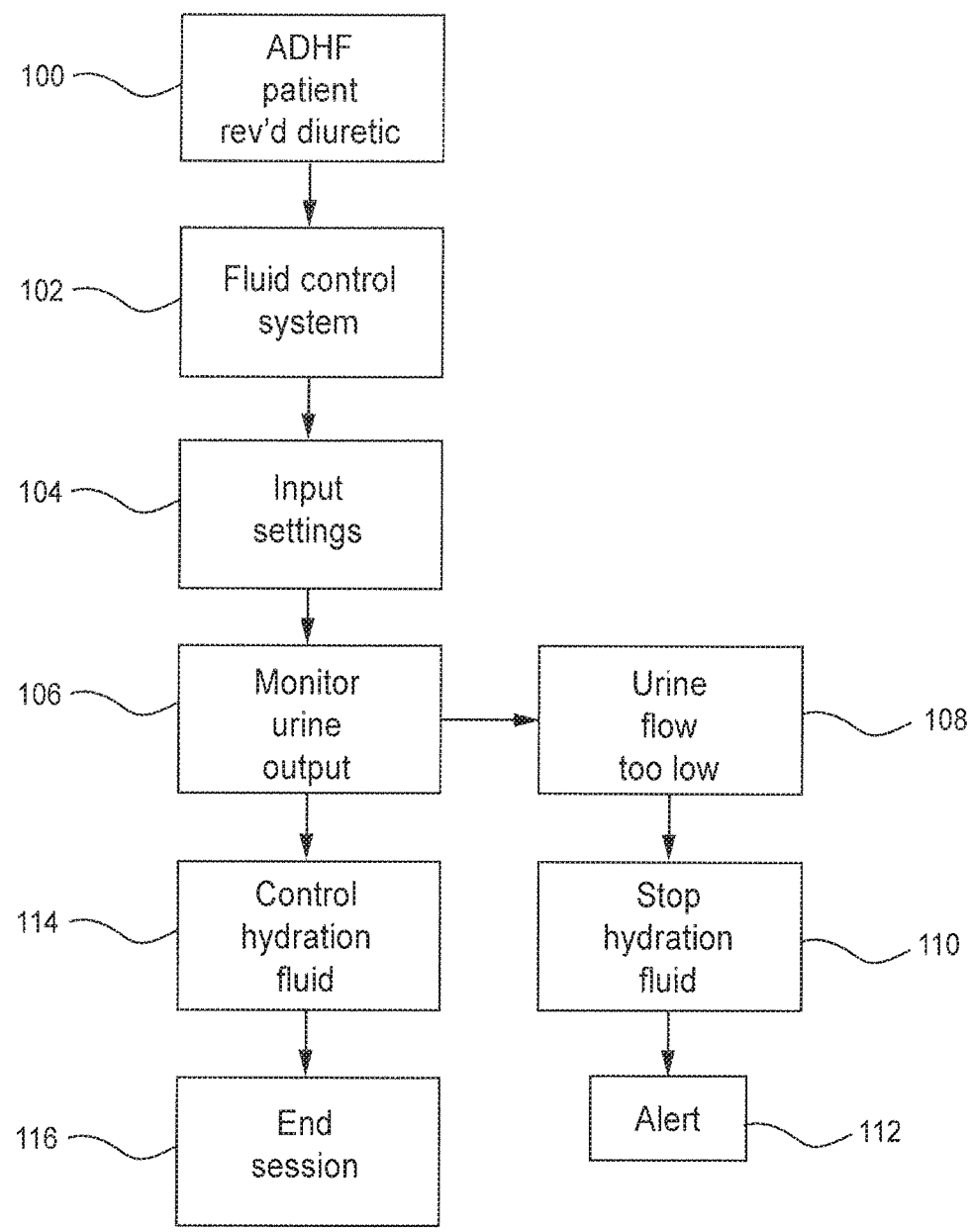
FIGS. 3 and 4 show a flow chart depicting one example of the steps processed by a controller and the logic used to determine and adjust the infusion rate based on the amount of urine output by the patient.

FIG. 3 shows an exemplary flow chart of a therapy session in which a patient suffering ADHF receives a diuretic and has fluid levels monitored. In step 100, the patient is diagnosed as suffering ADHF or other fluid overload condition. The patient is treated with a diuretic, such as by an IV line. The patient may be treated with diuretics and not connected to a fluid monitoring system for a certain period, such as twenty-four hours. During this period, the patient's urine output reduces the fluid level and thereby relieves some of the symptoms of ADHF. The treatment with diuretics before connecting the patient to a fluid control system is optional.

In step 102, the patient is connected to a fluid monitoring system, such as the RenalGuard® system. In connecting the patient, a Foley catheter is attached to the patient so that urine may be collected and measured. Similar, a source, e.g., saline filled bag, may be connected to the patient using an IV line. In step 104, settings are input to the fluid monitoring system, such as one or more of desired net urine output, period of session, desired net volume removal rate (which is the difference between infused fluid and urine output), and minimum urine output amount or rate. For example, the period may be twelve hours, eighteen hours, twenty-four hours, thirty hours or some other period set by the physician or other health care provider. The system may also be set to limit the amount of urine output or net volume removal rate to a certain maximum or minimum threshold, such as a net fluid loss of no more than 100 milliliters per hour (ml/hr) and at least 50 ml/hr. Similarly, the system may be set to detect a minimum urine output such as at least 30 ml/hr.

In step 106, the fluid control system monitors the urine output of the patient. The urine output is monitored during the entire treatment session. The monitoring of the urine output may include measuring the amount of urine output over time to determine a rate of urine output and a rate of net fluid loss. The net fluid loss is determined based on a difference between urine output and the amount of fluid infused into the patient. The computer control system 40 may repeatedly and automatically calculate the urine output rate during the treatment session. Knowing the urine output rate, the computer control system may determine the rate of hydration fluid to be infused, and whether to increase or decrease the rate of hydration fluid.

In step 108, the computer control system 40 determines if the urine output rate is too low. This determination may be made repeatedly during the treatment session, such as every 15 minutes, every 30 minutes, every hour or every few hours. The determination that the urine output rate is too low may be based on a comparison of the current urine output rate or amount to a lower threshold rate of urine output rate or amount. The lower threshold rate may be a minimum urine output rate at which the kidneys of the patient are adequately producing urine. A urine output rate below this minimum urine output rate indicates that the patient is not able to produce sufficient urine even when given diuretics and an infusion of hydration fluid.

In step 110, the fluid management system automatically stops the infusion of the hydration fluid in response to a determination, in step 108, that the urine output is too low. In step 112, the fluid management system generates an alert, such as a noise or a display image or alphanumeric indicating that the patient is not producing sufficient urine and/or the infusion of the hydration fluid has stopped. A physician may respond to the alert by treating the patient without other therapies, such as ultrafiltration, to treat the fluid overload condition.

If the urine flow is above the threshold applied in step 108, the fluid management system, in step 114, controls a rate at which the hydration fluid is pumped into the patient. The computer control system 40 may execute a program for pumping the hydration fluid which is intended to cause the patient to generate a high rate of urine. For example, the program may command a high rate of hydration fluid, such as shown in FIG. 2, during an initial period of the hydration fluid infusion and reduce, gradually or quickly, the rate of hydration fluid after the urine output rate reaches a desired threshold rate 62. The pumping rate may be set at a nominal rate, such as 10 ml/hr, to promote a high urine flow rate and reduced from that rate after the urine flow rate achieves the threshold rate 62. Also, the pumping rate of the hydration fluid may be automatically adjusted based on the rate or amount of urine output. For example, the pumping rate may automatically increase if the urine output rate falls below the threshold high urine rate 62.

The pumping rate of the hydration fluid may be automatically determined to achieve a desired net rate of negative overall fluid rate. For example, if the net rate of hydration fluid infused and urine output is at or near a desired net negative fluid reduction rate of 100 ml/hour, the pumping rate of the hydration fluid may remain constant. If the net negative rate is below a lower threshold rate (but above the rate in step 108) the rate of hydration fluid may be decreased. The lower threshold rate may be 90%, 80%, 75% or some other percentage of the desired net negative fluid reduction rate. Similarly, if the net negative rate is above an upper threshold rate, which indicates an excessively high urine rate, the pumping rate of hydration fluid may be increased.

In step 116, the fluid management system ends the treatment session by stopping the infusion of the hydration fluid. The treatment session may end based on a manual input from a physician, based on expiration of a time period as determined automatically by the fluid management system or based on achieving a desired net negative fluid balance amount as automatically determined by the fluid management system.

Figure 4:
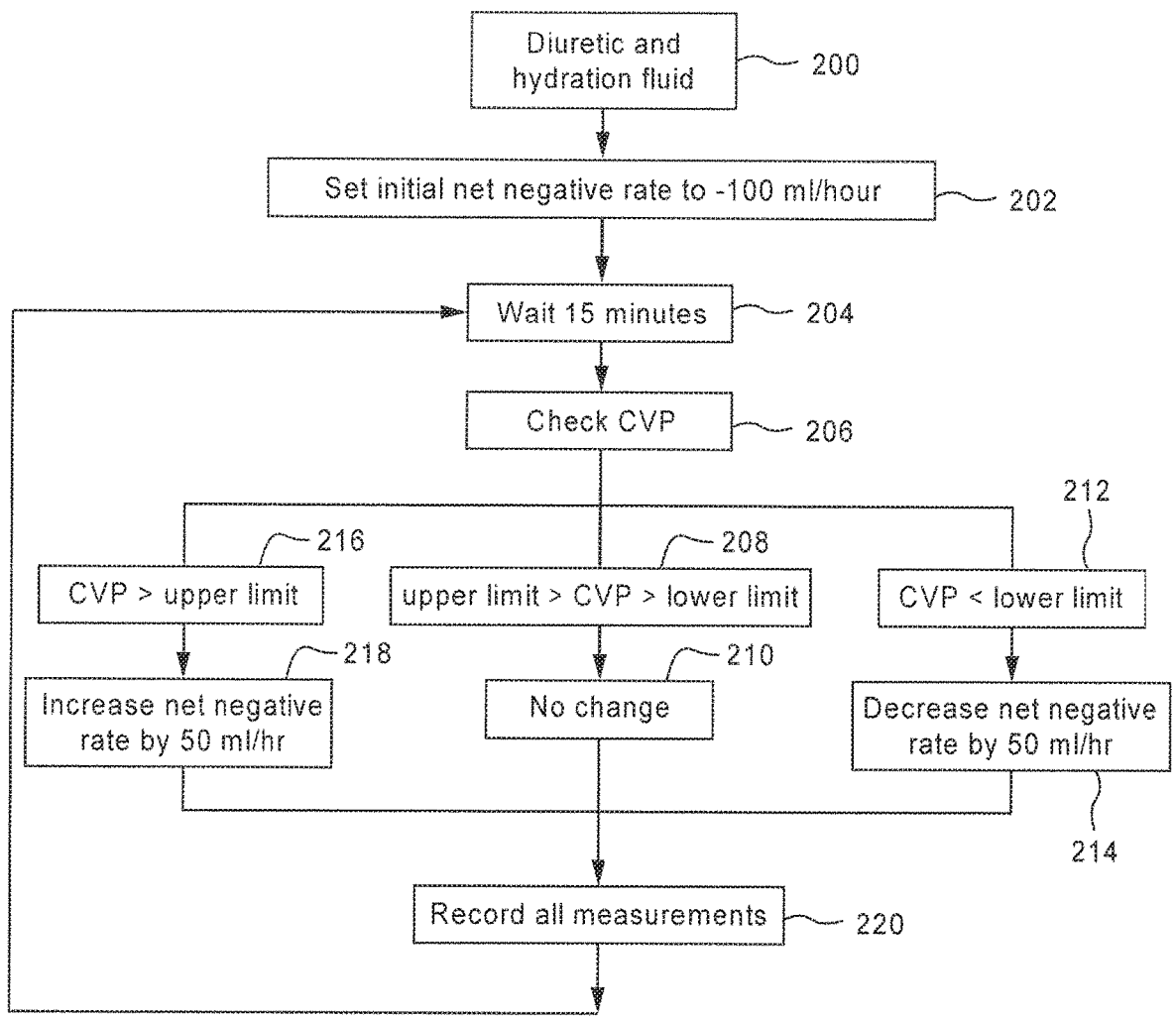

FIG. 4 is a flow chart showing an alternative technique to control the infusion of the hydration fluid in step 114. FIG. 4 shows measuring or estimating central venous pressure (CVP). CVP is an indicator of the intravascular fluid volume and can be used to determine settings for the net negative flow rate of hydration fluid infusion and urine output during a treatment session. One or more parameters of a patient may be monitored or measured to provide estimates or measurements of CVP.

In step 200, a patient diagnosed with ADHF or other fluid load condition is treated with a diuretic and connected to a fluid management system 10 to receive a hydration fluid. In step 202, the computer control system 40 is set to establish an initial negative fluid balance rate such as at a negative 100 ml/hour. This negative rate may be measured by the fluid management system based on a comparisons of the weight or rate of hydration fluid infused into the patient and the urine produced by the patient. A negative rate may be the difference between the rate or amount of urine produced and that of the infused hydration fluid. The fluid management system determines the current urine output amount or rate and adjusts the pumping rate of the hydration fluid to achieve the desired negative rate.

In step 204, the fluid management system may periodically, such as every 15 minutes during a treatment session, determine the CVP. The determination of the CVP, in step 206, may be measured using a central venous catheter connected to a pressure sensor or estimated from other parameters such as heart rate and blood pressure, urine output, chemicals in the urine, and using a Body Composition Monitor (BCM).

Using the CVP value determined in step 206, the fluid management system determines if the CVP is within a predetermined range in step 208. The range may be between upper and lower CVP values. If the CVP is within the range, the fluid management system may automatically continue to maintain the net negative rate at the same rate as was previously set in step 210. The net negative rate may be at the minus (−) 100 ml/hour initially set or another rate set by the system.

In step 212, if the CVP is below the range, the fluid management system reduces the net negative rate in step 214. Reducing the net negative rate may cause the fluid management system to automatically increase the pumping rate of hydration fluid such that the pumping rate is closer to the urine output rate. In step 216, if the CVP is above the range, the fluid management system increases the net negative rate in step 218, such as by reducing the pumping rate of the hydration fluid such that the pumping rate is further from the urine output rate. The changes to the net negative rate in 214 and 218 may be a step change of, for example, 50 ml/hour.

In step 220, the fluid management system records data indicating the CVP and whether the net negative rate was maintained, increased or decreased. In addition, the fluid management system returns to step 204 and waits for a certain period, such as 15 minutes, before again checking the CVP in step 206. The steps 204 to 220 are performed each period, until the end of the treatment session or until the fluid management system determines in step 108 that the urine output rate is too low.

Figure 5:
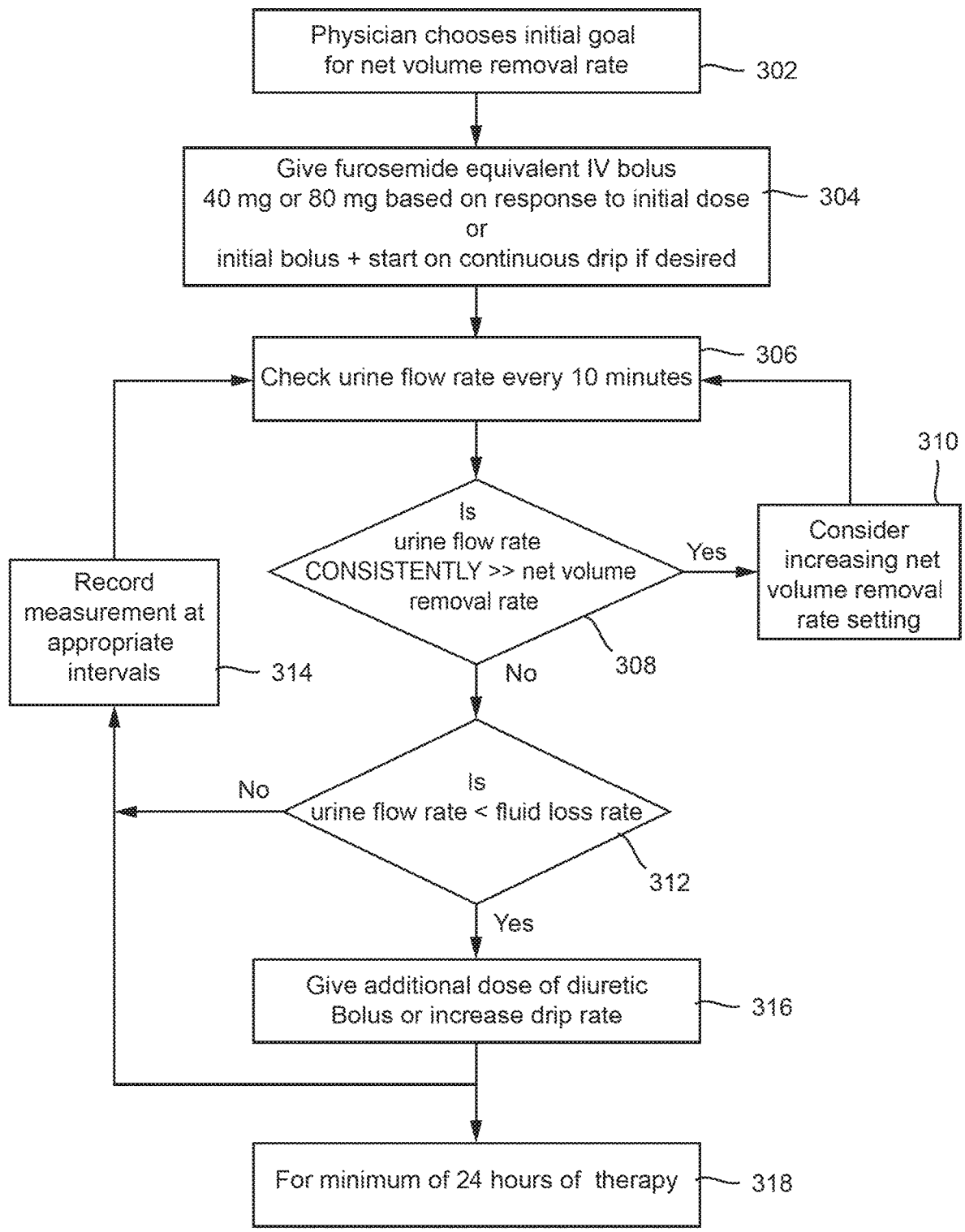
FIGS. 5 and 6 are flow charts showing exemplary treatment regimens.

FIG. 5 is a flow chart with an exemplary treatment regimen. The patient is connected to a fluid management system by an IV line to provide fluid for infusion and a Foley catheter to capture urine. A diuretic dose given to the patient may be a relatively large dose, such as the highest dosage levels recommended in guidelines or a dosage levels intended to create a urine output rate as high as the patient may safely tolerate. In step 302, a physician determines a goal for a net volume removal rate.

The net volume rate is a difference between a rate of fluid infusion and a rate of urine output. The goal for the net volume rate may be inputted into the fluid management system which may control the pumping rate of the infusion fluid to achieve the desired goal.

In step 304, the treatment is started by giving the patient a dose of a diuretic and may include infusing, e.g., dripping, the fluid into the patient at a rate determined by the controller of the fluid management system. The diuretic dose may be relatively high. In step 306, the controller regularly, such as every 10 minutes, determines the urine output rate based on a weight of urine output during a certain period or other urine fluid flow measurement. In step 308, the controller determines if the urine flow rate remains consistently, such as over one or more ten minute periods, at a level that is substantially, such as over 20%, above a rate needed to achieve the goal for the net volume removal rate. The determination of whether the urine flow rate is sufficient is determined by the controller as a difference of the rate of infusion fluid and rate of urine output.

If the urine flow rate is consistently substantially above a rate sufficient to meet the goal for net volume removal rate, the goal may be automatically or manually increased in step 310. If the urine output rate is not substantially above the rate needed to achieve the goal, the controller determines if the urine flow rate is at least greater than a rate needed to achieve the net volume removal rate (or some other minimum net fluid loss rate), in step 312. If the urine flow rate is greater than that needed to achieve the desired net volume removal rate, no change is made to the settings. Also, a record is made of the measurements (step 314), and the controller waits to re-check the urine flow rate in step 306.

If the urine flow rate is less than a rate needed to achieve the desired net fluid loss rate (step 312), the controller may automatically issue a prompt suggesting to a physician that dosage of the diuretic be increased and/or that the pumping rate be increased to increase the rate of the infusion liquid flowing to the patient, in step 316. The controller records measurements (step 314) and re-checks, every 10 minutes, the urine flow rate and repeats the steps (306 to 316) until the treatment session is completed, such as in 24 hours, in step 318.

Figure 6:
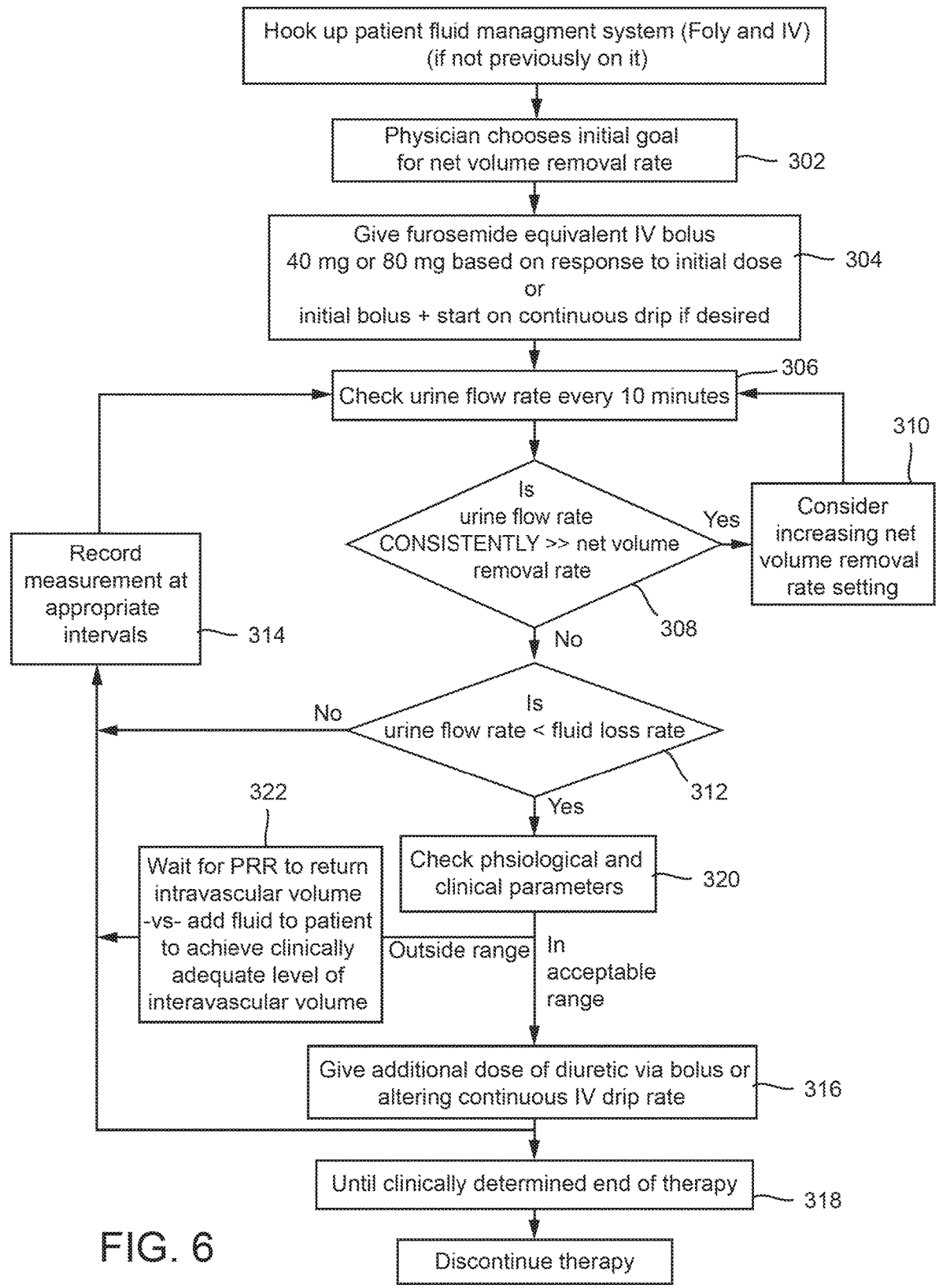

FIG. 6 is a flow chart of an exemplary treatment regimen similar to that shown in FIG. 5 except with additional steps. The steps in FIG. 6 similar to the steps in FIG. 5 are labeled with the same reference numbers.

In step 320, the patient's parameters, such as clinical and physiological parameters, are checked automatically by the controller, by another device or by a health care provider. This check is made if the urine flow rate is less than the desired net fluid loss rate. A determination is made whether the parameters are within or outside of acceptable ranges for the parameters. If outside the acceptable range(s), then there is a need to increase the patient's intravascular volume. Thus, a determination is made in step 322 of whether to increase the amount of infusion fluid or wait for the patient's plasma refilling rate (PRR) to increase the intravascular volume. The patient's parameters may be those that indicate a patient's CVP levels.

If the patient's parameters are within acceptable range(s), then the controller may increase the diuretic dosage given to the patient in step 316. By checking whether patient parameters are within acceptable ranges, the controller can first determine if the intravascular volume in the patient is at a sufficient fluid level to provide adequate kidney perfusion and supply needed fluids to other bodily organs.

The measured or estimated parameters of the patient may be useful to modify the treatment regime as the patient progresses through the treatment and to reduce the period needed to reach a desired net removal of fluid volume.

For example, at the beginning of therapy, there patient may have been a substantial amount of excess volume in the intravascular space as well as in the extravascular space that is able to move into the intravascular space in a time frame that will prevent excess intravascular volume depletion that may lead to undesired clinical and physiological consequences. In view of such substantial amount of excess volume, the regime may have a high desired net volume removal rate early in the course of therapy, such as during the first four hours, and a lower desired net volume removal rate during later portions of the therapy. Thus, a relatively high desired net volume removal rate may be set at the beginning of a treatment session and the rate is ramped down, such as linearly, during the course of the session as the fluid levels in the patient reach goals for total fluid removal. Towards the end of a session, the net volume removal rate may be reduced to a rate at which intravascular volume is maintained at clinically and/or physiologically acceptable levels.

In addition, a patient may have excessive amounts of urine or at a urine rate which is too high. If a determination is made that the urine amount or rate is too high, the urine output rate may be slowed by stopping or slowing, temporarily, the infusion of fluids or reducing the diuretic dosage. For example, the controller may gradually slow the infusion rate if the urine output rate is above an upper threshold for urine output.

In a trial of nine patients hospitalized with ADHF, all experienced greater amounts of fluid reduction through the use of a combination of a diuretic and the above described fluid treatment in which a hydration fluid was injected based on the amount of urine output. Each of the patients was initially treated with a diuretic (furosemide) for twenty-four hours Immediately following this initial treatment, each patient was connected to a fluid management system and continued to receive a diuretic for another twenty-four hours. Each of the patients reported significant improvement in dyspnea at the time of discharge from the hospital. There were no adverse events related to diuresis either with or without use of the fluid management system. A summary of the diuretic effects with and without the fluid management system are shown in Table A shown below:

TABLE 1

| Parameter | 24-hours Before RG Therapy | 24-hours with RG Therapy |
| --- | --- | --- |
| Total Dose of Furosemide (mg) | 85 ± 26 | 88 ± 35 |
| Total Urine (ml) | 2006 ± 1242 | 5116 ± 2299* |
| Diuretic efficiency (ml urine/40 mg furosemide) | 989 ± 571 | 2565 ± 1630* |

*$p < 0.01$

While the total dose of the diuretic was not significantly different with or without use of the fluid management system, the use of the fluid management system resulted in significantly improved therapeutic effects, including a two and one-half (2.5) multiple increase in the amount of urine. The patients were discharged from the hospital with marked weight reductions from 85±29 kg to 79±23 kg. The average change in estimated glomerular filtration rate (eGFR) at 30 days after the trial compared a baseline showed an average increase of 8% [range of +42% to −22%] with 3 (33%) patients by more than 25%, raising a potential for a long-term impact for this therapy. eGFR is an indicator of kidney health.

Although specific features of the invention are shown in some drawings and not in others, this is for convenience only as each feature may be combined with any or all of the other features in accordance with the invention. For example, there are other ways to determine a patient's urine output and other ways to quantify the amount of hydration fluid administered to the patient. There are also other ways to redundantly check the amount of hydration fluid administered the patient. Also, the words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

The invention claimed is:

1. A fluid management system, comprising:
a measurement system configured to measure urine output from a patient;
a pump configured to provide hydration fluid to the patient; and
a control system operatively coupled to the measurement system and the pump, the control system being configured to—
obtain a urine output rate based on the measured urine output from the measurement system;
receive a desired net fluid loss rate for the patient;
during a first period, cause the hydration fluid to be provided, via the pump, to the patient at a hydration fluid rate; and
during a second period after the first period, and based on at least one of the urine output rate or the desired net fluid loss rate, adjust operation of the pump to increase the hydration fluid rate.

2. The fluid management system of claim 1, wherein the control system is further configured to obtain an amount of diuretic or a diuretic dosage rate provided to the patient.

3. The fluid management system of claim 2, wherein adjusting operation of the pump is further based on the obtained amount of diuretic or diuretic dosage rate.

4. The fluid management system of claim 1, wherein the control system is further configured to cause a diuretic to be provided to the patient at a diuretic dosage rate.

5. The fluid management system of claim 1, wherein the control system is further configured to provide an indication that a diuretic dosage rate is to be increased, based on the obtained urine output rate being below a threshold rate.

6. The fluid management system of claim 1, wherein the control system is further configured to obtain an actual net fluid loss rate based at least in part on the urine output rate and the hydration fluid rate, and wherein adjusting operation of the pump to increase the hydration fluid rate is based on a difference between the desired net fluid loss rate and the actual net fluid loss rate.

7. The fluid management system of claim 1, wherein the desired net fluid loss rate is at least 50 milliliters/hour.

8. The fluid management system of claim 1, wherein causing the hydration fluid to be provided to the patient at the hydration fluid rate is based at least in part on the urine output rate relative to a predetermined threshold urine rate or amount.

9. The fluid management system of claim 1, wherein the control system is further configured to adjust operation of the pump to decrease the hydration fluid rate, based on the obtained urine output rate being above a threshold rate.

10. The fluid management system of claim 1, wherein adjusting operation of the pump to increase the hydration fluid rate is based on the obtained urine output rate being below a threshold rate.

11. The fluid management system of claim 1, wherein adjusting operation of the pump to increase the hydration fluid rate is based on both the urine output rate and the desired net fluid loss rate.

12. The fluid management system of claim 1, further comprising a blood pressure monitor operatively coupled to the control system, wherein the control system is further configured to monitor a blood pressure of the patient, via the blood pressure monitor, while causing the hydration fluid to be provided.

13. The fluid management system of claim 12, wherein adjusting operation of the pump to increase the hydration fluid rate is further based on the monitored blood pressure.

14. A method for managing fluid levels in a patient, the method comprising:
obtaining a urine output rate from a patient;
receiving a desired net fluid loss rate for the patient;
during a first period, cause the hydration fluid to be provided, via the pump, to the patient at a hydration fluid rate; and
during a second period after the first period, and based on at least one of the urine output rate or the desired net fluid loss rate, adjust operation of the pump to increase the hydration fluid rate.

15. The method of claim 14, further comprising obtaining an amount of diuretic or a diuretic dosage rate provided to the patient, wherein adjusting operation of the pump is based on the obtained amount of diuretic or diuretic dosage rate.

16. The method of claim 14, further comprising causing a diuretic to be provided to the patient at a diuretic dosage rate.

17. The method of claim 16, wherein causing the hydration fluid to be provided occurs after causing the diuretic to be provided to the patient at the diuretic dosage rate.

18. The method of claim 14, further comprising:
   determining that the obtained urine output rate is below a threshold rate; and
   providing an indication that the urine output rate is below the threshold rate.

19. The method of claim 14, further comprising obtaining an actual net fluid loss rate, wherein adjusting operation of the pump to increase the hydration fluid rate is based on a difference between the desired net fluid loss rate and the actual net fluid loss rate.

20. The method of claim 14, wherein the urine output rate is above a threshold rate, the method further comprising adjusting operation of the pump to decrease the hydration fluid rate.

* * * * *

UNITED STATES PATENT AND TRADEMARK OFFICE
CERTIFICATE OF CORRECTION

PATENT NO. : 12,239,819 B2  
APPLICATION NO. : 17/056387  
DATED : March 4, 2025  
INVENTOR(S) : Howard R. Levin et al.

Page 1 of 1

It is certified that error appears in the above-identified patent and that said Letters Patent is hereby corrected as shown below:

On the Title Page

On the page 4, in Column 1, under item (56) "Other Publications", Line 25, delete "Pharmcokinetics," and insert -- Pharmacokinetics, --.

On the page 4, in Column 2, under item (56) "Other Publications", Line 35, delete "Iohexol," and insert -- iohexol, --.

On the page 5, in Column 1, under item (56) "Other Publications", Line 9, delete "Urogyecologyl" and insert -- Urogynecology --.

On the page 5, in Column 2, under item (56) "Other Publications", Line 11, delete "Furosmide" and insert -- Furosemide --.

On the page 5, in Column 2, under item (56) "Other Publications", Line 13, delete "Univeristy" and insert -- University --.

In the Specification

In Column 1, Line 53, delete "decompentated" and insert -- decompensated --.

In the Claims

In Column 12, Line 61, in Claim 14, delete "cause the" and insert -- causing --.

In Column 12, Line 62, in Claim 14, delete "the pump," and insert -- a pump, --.

In Column 12, Line 66, in Claim 14, delete "adjust" and insert -- adjusting --.

Signed and Sealed this  
Twenty-ninth Day of April, 2025

Coke Morgan Stewart  
*Acting Director of the United States Patent and Trademark Office*